United States Patent [19]

Dole et al.

[11] Patent Number: 4,978,502

[45] Date of Patent: Dec. 18, 1990

[54] IMMUNOASSAY OR DIAGNOSTIC DEVICE AND METHOD OF MANUFACTURE

[75] Inventors: Charles M. Dole, Purdys, N.Y.; Gary L. Webster, Fairfield, Conn.; Ward C. Smith, Mahwah, N.J.

[73] Assignee: Dole Associates, Inc., Katonah, N.Y.

[21] Appl. No.: 130,616

[22] Filed: Dec. 15, 1987

Related U.S. Application Data

[63] Continuation-in-part of Ser. No. 439, Jun. 5, 1987, Pat. No. 4,769,333.

[51] Int. Cl.$^5$ .......................... G01N 22/00; B01L 3/00
[52] U.S. Cl. ......................... 422/58; 422/102; 435/810; 436/808; 436/809
[58] Field of Search ................... 435/7, 810, 287, 299, 435/300, 301, 311; 422/56, 57, 58, 61, 68, 101, 102; 436/808, 809, 65, 510; 222/83, 81; 206/569, 603; 30/124

[56] References Cited

U.S. PATENT DOCUMENTS

| | | | |
|---|---|---|---|
| 3,355,069 | 11/1967 | Miles | 222/83 |
| 3,476,515 | 11/1969 | Johnson et al. | 422/61 X |
| 3,497,320 | 2/1970 | Blackburn et al. | 422/102 X |
| 3,657,073 | 4/1972 | Burton et al. | 435/31 X |
| 3,689,224 | 9/1972 | Agnew et al. | 422/61 |
| 3,776,220 | 12/1973 | Monaghan | 435/295 X |
| 3,799,742 | 3/1974 | Coleman | 422/102 X |
| 3,986,834 | 10/1976 | Steibrink, Jr. | |
| 4,129,483 | 12/1979 | Bochner | 435/301 X |
| 4,246,339 | 1/1981 | Cole et al. | 435/7 |
| 4,298,035 | 11/1981 | Hossom | 435/32 X |
| 4,324,758 | 4/1982 | Eisentraut et al. | 422/61 |
| 4,366,241 | 12/1982 | Tom et al. | 435/7 |
| 4,428,506 | 1/1984 | Withey | 222/83 X |
| 4,428,907 | 1/1984 | Heijenga et al. | 422/61 |
| 4,458,020 | 7/1984 | Bohn et al. | 436/810 X |
| 4,549,655 | 10/1985 | Forsythe, Jr. et al. | 206/569 |
| 4,632,901 | 12/1986 | Valkirs et al. | 435/5 |
| 4,665,034 | 5/1987 | Chandler | 436/808 X |
| 4,690,801 | 9/1987 | Anderson | 422/68 |
| 4,708,850 | 11/1987 | Husain | 422/68 X |

FOREIGN PATENT DOCUMENTS

| | | |
|---|---|---|
| WO86/06488 | 11/1986 | PCT Int'l Appl. . |
| 1331503 | 9/1973 | United Kingdom . |
| 2002316A | 2/1979 | United Kingdom . |

*Primary Examiner*—Christine Nucker
*Attorney, Agent, or Firm*—Bachman & LaPointe

[57] ABSTRACT

Liquid containers or receptacles are disclosed with cooperating means for rupturing the receptacles to release contained fluid to rain upon test specimens. Structure is disclosed for rupturing receptacles in response to relative motion occurring between receptacles and test specimen support members or in response to punch means formed integrally with a receptacle. A method of molding a liquid receptacle with an integrally formed punch means for rupturing the receptacle is also disclosed.

4 Claims, 5 Drawing Sheets

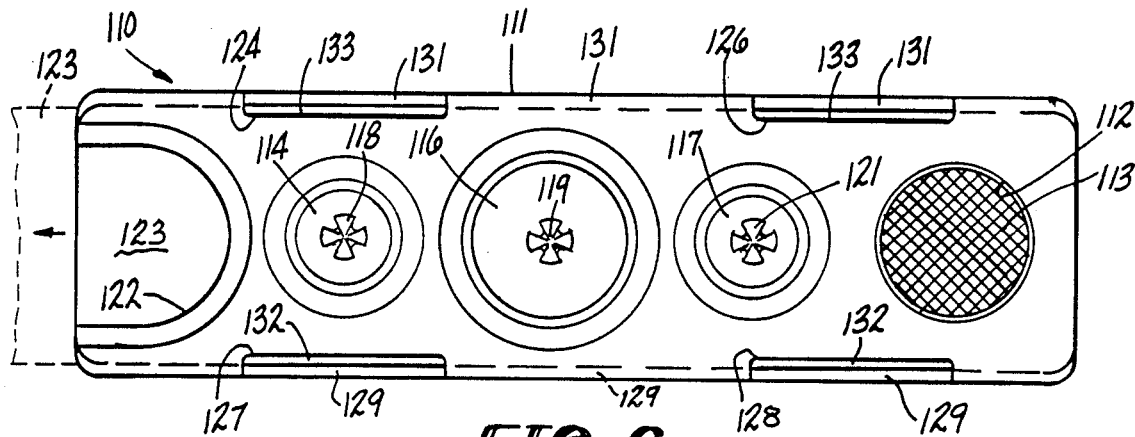
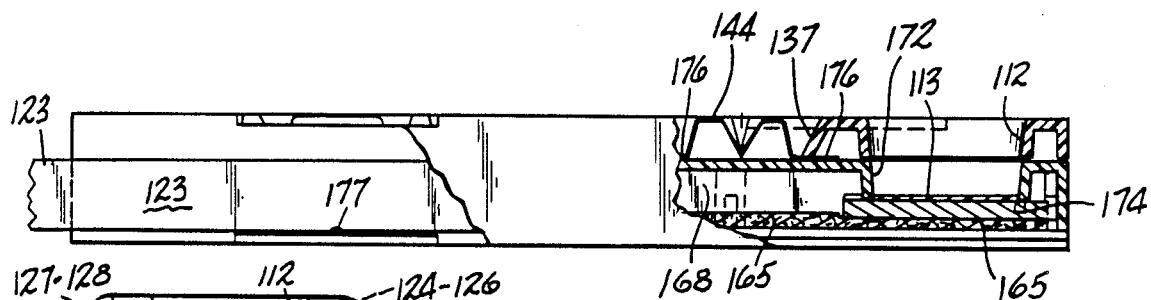
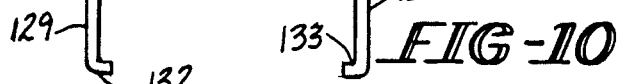
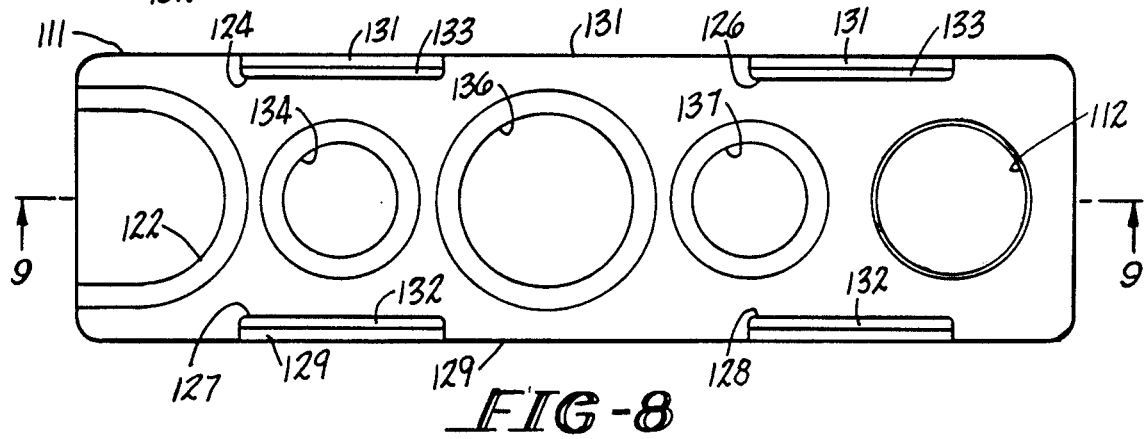
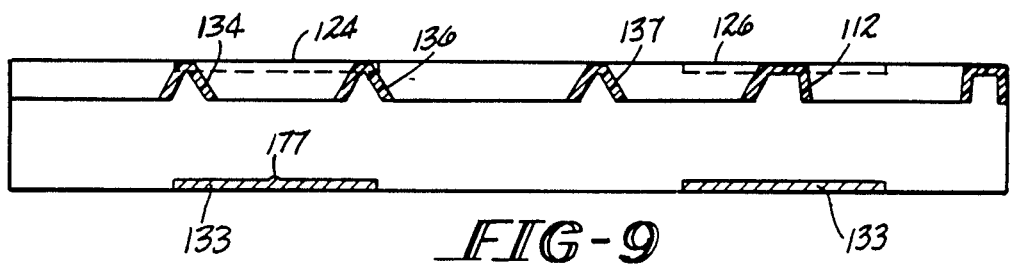

4,978,502

IMMUNOASSAY OR DIAGNOSTIC DEVICE AND METHOD OF MANUFACTURE

CROSS REFERENCE TO RELATED APPLICATION

This application is a Continuation-In-Part of co-pending U.S. patent application Ser. No. 000,439, filed Jan. 5, 1987, now U.S. Pat. No. 4,769,333, by Charles M. Dole et al., entitled PERSONAL DIAGNOSTIC KIT.

BACKGROUND OF THE INVENTION

The present invention relates to assay or diagnostic devices and relates in particular to disposable, hand held units useful to make relatively immediate tests, assays or diagnoses.

The invention also relates to a method of manufacturing a liquid receptacle or container with an integrally formed punch means for rupturing the container.

Typical prior art devices are disclosed in U.S. Pat. Nos. 3,986,834, 4,162,003, 4,175,008, 4,549,655, 4,608,231, 4,428,907 and 4,632,901.

The '834 patent shows a series of reagent bottles 14 received in a tray 12 where the bottles contain a frangible capsule 20.

The '003 patent shows a plurality of bottles 1 and 6 having a separate compartment 5.

The '008 patent shows a specimen collector and transport test tube 10.

The '655 patent shows relatively rotatable elements 14 and 16 for registering openings 20 and 34 with layered stack 12.

The '231 patent shows a bracket unit 10 for supporting a plurality wells such as well 14.

The '907 patent shows piercing pins 5 for piercing container 20.

The '901 patent shows an immunoassay unit fixed in a tubular housing.

SUMMARY OF THE INVENTION

In contrast, the present invention deals with a compact, hand held, contamination free, disposable or diagnostic device which is very easy to operate and produces meaningful results in rapid fashion.

It is a further feature of the invention to provide a composite device whose size and configuration lends itself economically to modern high speed mass production methods using appropriate synthetic moldable compounds.

A further feature of the invention is the provision of a device of the type described which includes a plurality of receptacles for containing fluid reagents or other liquid materials including water with means for releasing fluids selectively to react upon a test specimen.

A further feature of the invention is the provision of a diagnostic, assay or test device which, by virtue of its structure, is operable to perform a number of useful functions providing results that are meaningful to the ordinary layman.

A still further feature of the present invention is the provision of a device of the type described which is self contained and whose operation is performed personally by the user without the need for technical or professional supervision or assistance.

A further feature of the invention is that groups of devices can be "loaded" or charged at the point of manufacture where each group is designated to perform a specific test, assay or diagnosis.

For example, one group of devices may be available commercially as a pregnancy test.

Another group of devices may be charged with reagents or fluid materials for identifying the existance of particular bacteria, virus, or other identifiable material.

A further group of devices may be charged with reagents or materials useful in veterinary applications.

A further feature of the invention is the provision of a novel linear arrangement or an arcuate array of receptacles for containing liquid materials where rupture means are provided for releasing said liquids sequentially for reaction with a test specimen; all liquid materials are contained at all times within the device in a neat and tidy fashion.

A further feature of the invention is the provision of a device including at least one liquid container and a punch means for rupturing the container where the punch means and the container are unitary and the punch means makes a seamless connection with the container.

A still further feature of the invention is the method of manufacturing the container and the punch means in seamless, unitary fashion.

A further feature of the invention is the provision of a plurality of liquid containers and at least one test specimen support means including means for indexing the specimen support means relative to said container in step by step fashion.

A further feature of the invention is the provision of structure permitting indexing to occur along a circular or along a linear path.

A diagnostic device embracing certain principles of the invention may comprise a support member for suspending at least one receptacle containing liquid material and a cutting means operatively connected to said support member, said support member and said cutting means being movable relative to one another whereby said cutting means is operable to shear, slit or rupture said receptacle to release said liquid material in response to relative motion.

A device embracing certain other features of the invention may comprise a housing means supporting at least one liquid container, a movable test specimen support means, track means in said housing for supporting and guiding said specimen support means into register with said container and manually operable rupture means formed integrally and seamlessly with said container for releasing fluid from said container to said specimen support means.

A method of fabricating a container having an integrally formed seamless connection with a punch means involves the use of a sheet of thermoplastic material. Providing a mold in the reverse image of the container and the punch means. Heating the sheet to a moldable temperature and thereafter drawing the sheet into contact with the mold by a suitable procedure such as the well known vacuum forming technique to form a blister which includes the punch means configuration thereafter sealing the blister with a sheet of foil or film to complete the container.

For purposes of interpreting claims, the term "liquid" is intended to include flowable solid material in granular or particulate form.

BRIEF DESCRIPTION OF THE DRAWINGS

Other features and advantages of the present invention will become more apparent from an examination of the succeeding specification when read in conjunction with the appended drawings, in which;

FIG. 6 is a plan view of an alternative embodiment of the diagnostic device in a linear arrangement in contrast to the circular arrangement of FIGS. 1 and 2, FIG. 7 is a side elevation of FIG. 6 partially in section, FIG. 8 is a top plan view of a blister pack matrix or device housing, FIG. 9 is a vertical section of FIG. 8 in the plane of the line 9—9, FIG. 10 is an end view of the right end of FIG. 8.

DETAILED DESCRIPTION OF THE INVENTION

Figure 1:
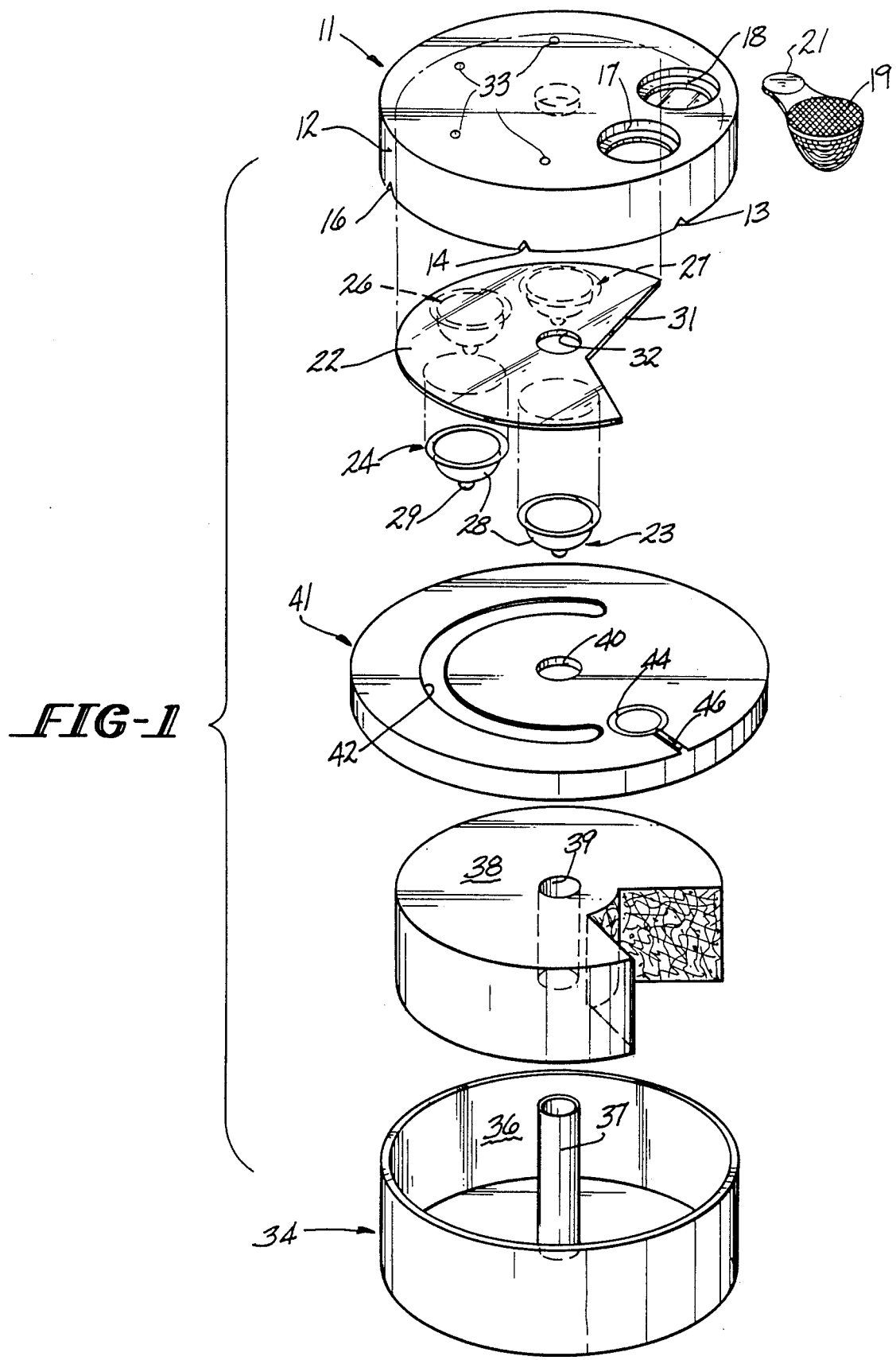
FIG. 1 is an exploded view of the basic elements of one embodiment of the diagnostic device of the present invention.

Referring in detail to FIG. 1, a first housing member 11 formed with a skirt 12 having V-shaped notches 13, 14, and 16 (first dententing means) is further formed with a specimen access opening 17 and a viewing access opening 18. The specimen access opening 17 is operable to receive a funnel-filter 19 having a finger tab 21 in the event a test specimen introduced into opening 17 contains solid or agglomerate matter which must be retained or removed.

Below the first housing member 11 is circular sector 22 which serves as a support member for a plurality of liquid tight containers or receptacles 23, 24, 26, and 27 having a body portion 28 and a nipple portion 29.

The sector 22 includes a cut-out 31 and a central opening 32 whose purpose and function will become more apparent as the specification proceeds.

The receptacles 23 through 27, fabricated or molded individually from a suitable light gauge synthetic plastic which cuts or shears readily, are filled with liquid materials appropriate to the particular test, assay, or diagnosis procedure and are secured to the underside of the sector 22 by a suitable adhesive or by high frequency heating, as desired.

The sector 22 and the suspended liquid receptacles 23 through 27 are secured to the underside of the first housing member 11 in suitable fashion. Alternatively, the sector 22 can be eliminated and, in that situation, the receptacles are secured to the underside of the first housing member 11 directly.

Thus, the underside of the housing member 11 becomes the receptacle support member. In this event the housing member 11 may be provided with small sealable access openings as indicated by circles 33—33 for loading or charging the receptacle's using an appropriate syringe device.

As a further alternate, the receptacles may be formed as a group (vacuum formed, for example) from a sheet of suitable plastic material where all receptacles are joined or are interconnected by margins between receptacles in linear, circular or random array. After filling each receptacle with the material appropriate to the test, a sealing film is placed over the formed sheet covering and sealing each receptacle and the margins.

Thereafter, the formed, filled, and sealed sheet is secured by suitable means to the underside of the first housing member. In this case no access openings 33 are needed.

A second housing member 34 having an upstanding skirt 36 formed with a central pin or axle 37 receives an absorbant pad 38 having a clearance opening 39 for the axle 37.

The axle, providing a central bearing for a rotary cutting means 41, passes through aperture 40 and aperture 32 of sector 22 and bottoms in an internal socket 35 in first housing member 11. The axle is fixed to the housing member 11 by appropriate means with adequate clearance to permit relative motion between the cutting means 41 and the assembled first and second housing members in a manner and for a purpose that will become apparent hereinafter.

The cutting means 41 is shaped in the form of a disc of a diameter somewhat larger the the diameter of the housing members and is knurled or roughened at its periphery to facilitate grasping manually.

The cutting means or disc 41 is formed with a through slot 42 of an arcuate configuration complementary to the arcuate array of the nipples 29 of the receptacles 23, 24, 26, and 27. The slot 42 receives and provides clearance for the nipples 29 as is most apparent in FIG. 3.

The right extremity of the slot 42 terminates in a knife or cutting edge 43 and immediately adjacent the cutting edge is a support element 44 for receiving a test specimen. The specimen support element 44 may take the form of a wafer or a membrane including a permeable or treated membrane as test, assay or diagnostic procedures require.

The cutting means or disc 41 is formed further with a rib or detent 46 (second detent means) projecting and disposed centrally relative to the specimen support element 44. The detent 46 cooperates with notch 13 of first housing member 11 (aligned with specimen access opening 17) to lock the disc 41, releasably, with the specimen access opening 17 in register with the specimen support element 44.

OPERATION

Figure 2:
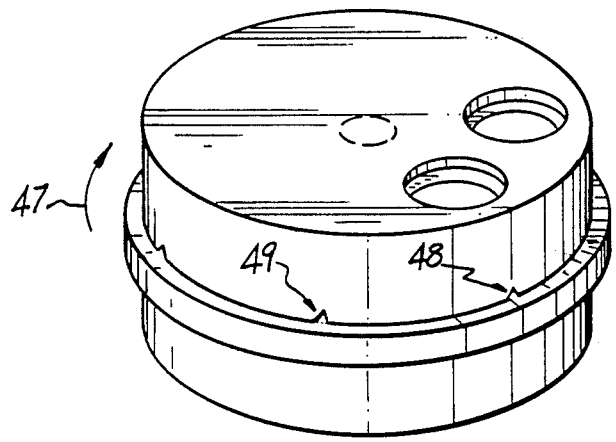
FIG. 2 is a perspective view of the assembled device.

Operation of the device occurs as follows:

Assume that the device is assembled as shown in FIG. 2 with the specimen access opening 17 in releasable register with the specimen support element 44 and with the several receptacles 23, 24, 26, and 27 having been charged or loaded at the point of manufacture with liquid material appropriate to the test, assay or diagnosis for which the device is intended. In addition, assume that the specimen support element 44 has been inoculated or coated with a specimen by the user (consumer) using filter-funnel 19 or swab 52 and swab holder 51, as appropriate.

At this time the nipples are received in the arcuate slot 42 clear of the knife 43 and each receptacle is aligned individually with notches 13, 14 and 16. That is, receptacle 28 is aligned with notch 14 and so forth.

The individual user grasps the housing firmly (the first housing member 11 or the second housing member 34 or both members) and rotates the disc 41, in the direction of the arrow 47 of FIG. 2, relative to the housing.

This occurrence breaks or releases the detent lock at 48 FIG. 2 and the disc 41 and its detent 46 are moved relative to the housing until the detent 46 snaps into the next housing notch at 49.

Figure 3:
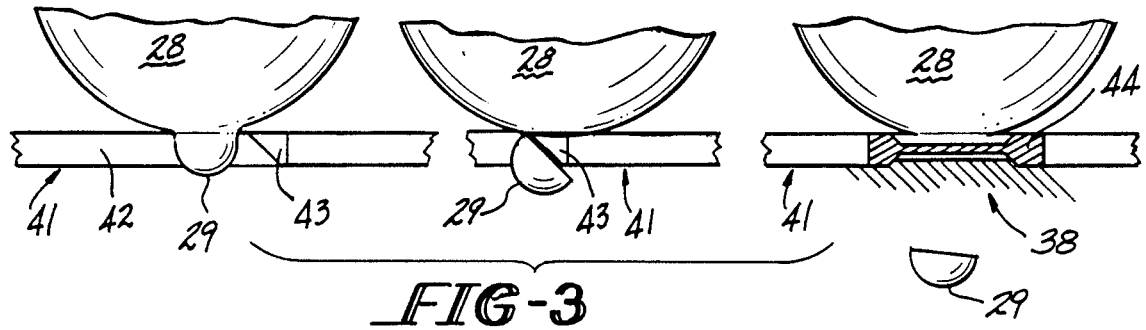
FIG. 3 is a schematic illustration of the rotary disc its cutting element, the shearing sequences and the test specimen support element or wafer.

During the course of this relative rotation the knife 41 operates to shear nipple 29 (see FIG. 3) from its mating receptacle 28 to release fluid material. The location of detent means (notch at 49 FIG. 2) on the skirt 12 of the first housing member insures that the material from receptacle 28 released rains or plays upon the test specimen as shown in FIG. 3.

Absorbant pad 38 is of sufficient thickness to wipe the underside of the disc 41 to absorb any excess fluid material and to draw fluid through a porous membrane.

After an appropriate interval and in accordance with instructions supplied for the particular test, assay, or diagnostic procedure the disc 41 is rotated to the next detent lock, a nipple is sheared, and the test specimen is again showered with liquid material from a second receptacle.

Obviously the number of receptacles 23, 24, 26, and 27 is not critical to the present invention, so long as there are sufficient reagents including water available for the particular test, assay or diagnosis for which the device is intended.

It is also well to point out that although the relative motion described in connection with the exemplary embodiment of the invention is rotary it is entirely within the spirit and scope of the invention that the relative motion be linear or part rotary and part linear so long as relative motion between the knife and the receptacles operates to slit receptacles sequentially to release liquid to treat a test specimen.

Figure 4:
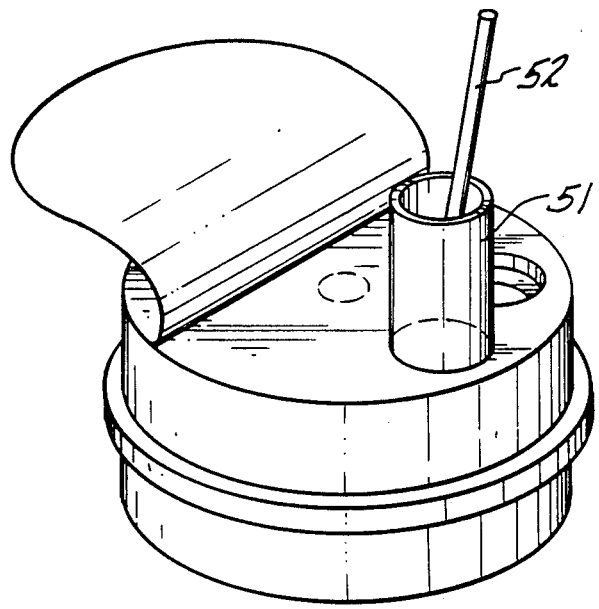
FIG. 4 is a perspective illustration of the assembled device showing a swab and swab holder for introducing a test specimen to said specimen support element of FIG. 3.

FIG. 4 shows an alternative scheme for introducing a test specimen to the specimen support element 44 in that swab holder 51 and a swab 52 are used in lieu of in the funnel-filter 19 of FIG. 1.

Frequently it is desirable to intermix two different liquid materials just prior to personal use of the device. These are situations where, for example, premature co-mingling of liquids would reduce or eliminate their efficacy.

Figure 5:
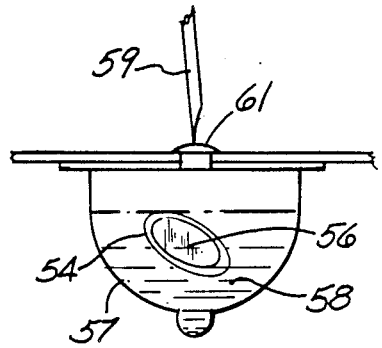
FIG. 5 is a schematic illustration of a liquid receptacle containing a capsule-like secondary liquid container including a needle-like probe for rupturing said secondary container to release its liquid.

In such situations arrangements such as shown in FIG. 5 are devised. A rupturable capsule 54 containing a fluid material 56 is disposed in a selected receptacle 57 containing fluid material 58.

At the appointed time prior to personal use of the device and in accordance with instructions a needle-like probe 59 is inserted through a rupturable cap 61 rupturing the capsule to release its fluid to co-mingle with the receptacle fluid.

Thus, when the disc 34 is rotated to the detent means corresponding to the receptacle 57 the mixed fluid material rains upon the specimen in the manner described previously.

ALTERNATIVE EMBODIMENT

Referring to FIGS. 6 through 18, an alternative embodiment of the test, assay or diagnostic device is shown at reference number 110 in FIG. 6 which is arranged to operate in linear fashion in contrast to the rotary action of the device of FIGS. 1 through 5.

The linearly arranged device includes a housing 111 having an opening 112 Providing access to a specimen support means 113. The specimen support means can take the form of a membrane, filter or a wafer depending upon the particular test for which the device is designated at the point of manufacture.

A plurality of liquid containers 114, 116 and 117 each having a manually operable punch or rupture means 118, 119 and 121, respectively are shown nested or received in the housing. Obviously the invention is not limited to the size and number of the containers shown. Three containers are merely representative of the inventive concept.

While the disclosed alternative embodiment of the invention, shown in FIGS. 6 through 18 illustrates a linear arrangement of liquid containers 114, 116 and 117, it is entirely within the spirit and scope of this embodiment that the containers be disposed in an arcuate or circular array or in a part linear and part arcuate or in a random arrangement.

The housing is formed further with an additional access opening 122 facilitating the manual grasping and indexing of a specimen conveyor means 123 in a manner and for a purpose which will become more apparent as the specification develops.

For convenience in molding, the housing 111 is formed with cut-outs 124, 126, 127 and 128 revealing housing side walls 129 and 131 as well as contiguous inwardly projecting track means 132—132 and 133—133 (see FIG. 10) for guiding conveyor means 123 as it is moved manually relative to the housing.

As is more apparent in FIGS. 8 and 9, the housing 111 is formed further with tapered openings 134, 136 and 137 for receiving the containers 114, 116 and 117 in nested fashion.

Figure 11:
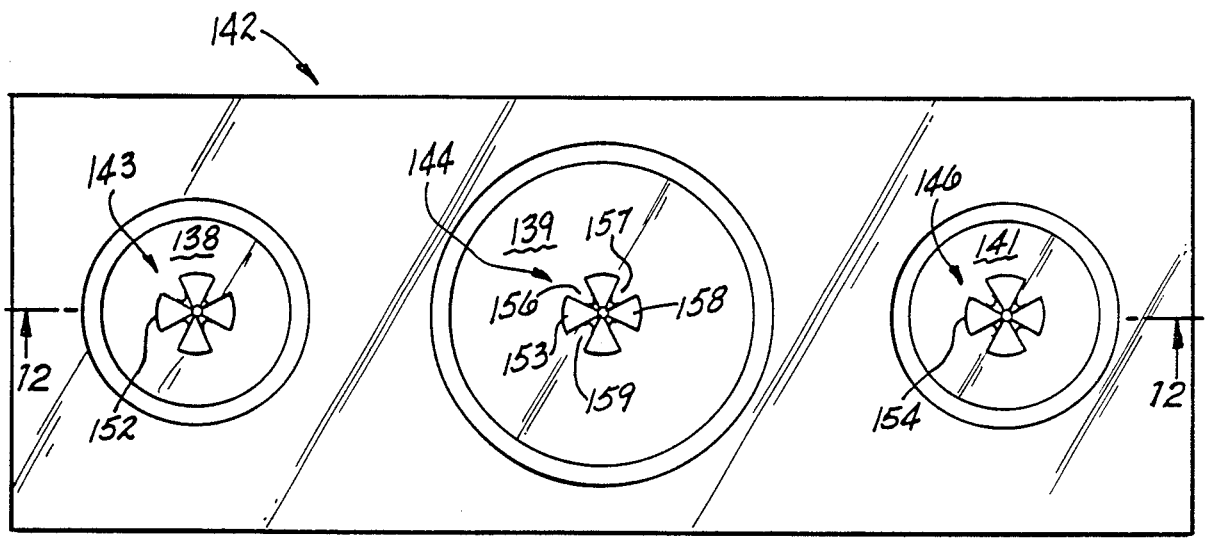
FIG. 11 is a top plan view of the liquid reagent blister pack.
Figure 12:
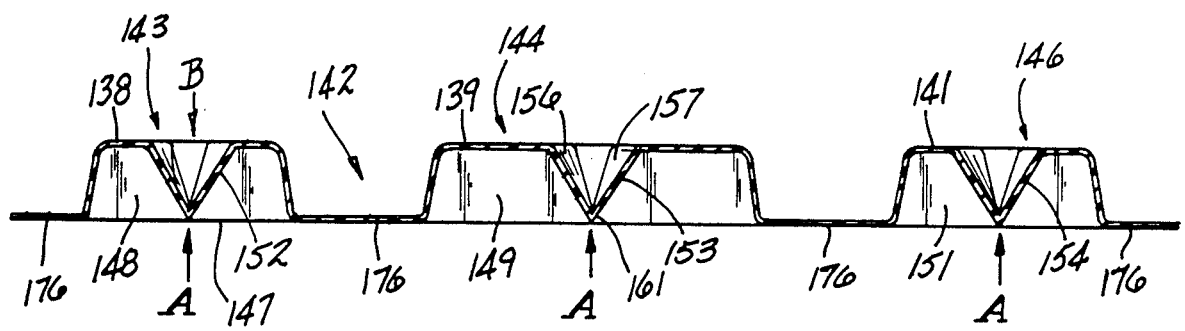
FIG. 12 is a vertical section of FIG. 11 in the plane of line 12—12.

The containers are fabricated from a blister pack indicated generally ar 142 in FIGS. 11 and 12. The blister portions 138, 139 and 141 of the pack 142 are fabricated from a sheet of moldable, flexible plastic material drawn over a mold of a reverse image by well known procedures such as vacuum forming. Each blister includes an integral, seamless punch identified generally by the reference numerals 143, 144 and 146.

At the point of manufacture the blisters 138, 139 and 141 are inverted (relative to the position of FIG. 12), filled with liquid or reagent (as desired) and then sealed by a foil or film 147 to define liquid tight fluid receptacles 148, 149 and 151.

As is most apparent in FIGS. 11 and 12, the punch means 143, 144 and 146, formed integrally and seamlessly with a mating blister 138, 139 and 141, respectively, define a fluted generally cone-shaped configuration. The exterior lateral surfaces 152, 153 and 154 of each is interrupted by a plurality of graduated, concave indentations or grooves, for example, grooves 156, 157, 158 and 159 of punch means 144 in FIG. 11. The grooves, arranged in a northeast-southwest and northwest-southeast pattern, extend from the base B of the cone shape to the apex A. The grooves are of greatest depth at the base of the cone and gradually decrease in depth as they extend toward the apex until the grooves finally "run out" at the apex to define a sharp point.

The number of grooves, the graduation rate, depth and disposition is a matter of engineering choice and design and it is nor intended that the punch means or the number of liquid tight containers be limited to the disclosed exemplary embodiment of the invention.

The specimen support 113 and its transport or conveyor means 123 is disclosed and described in FIGS. 13, 14, 15 and 16. The conveyor means 123 comprises two basic elements, namely base plate 162 and top plate 163. These plates are fastened together by any suitable means and form an interior void or core for reception of an absorbant. In the disclosed embodiment, guide pins 164—164 of base plate 162 make a press fit into mating bores 166—166 formed in posts 167—167 which depend from top plate 163.

Figure 13:
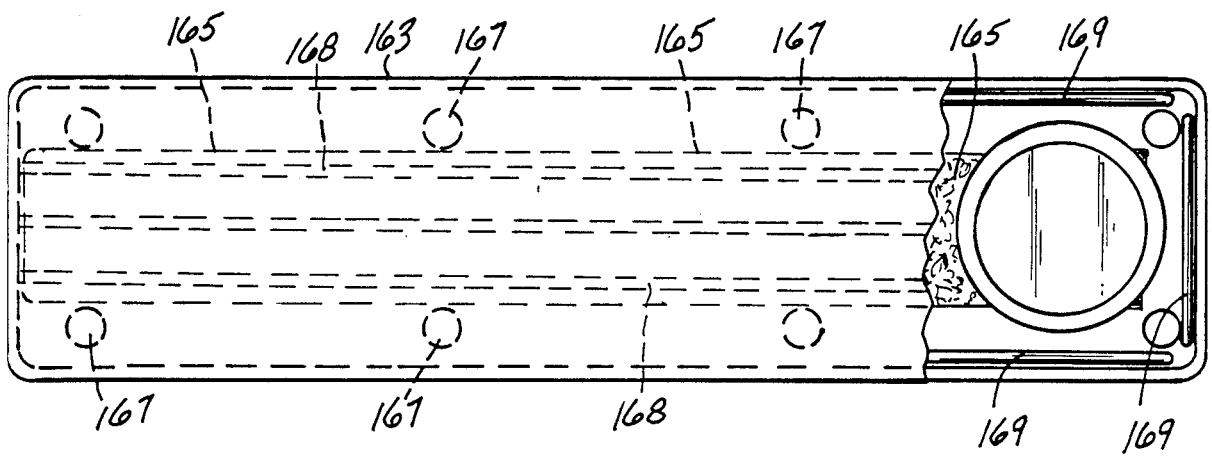
FIG. 13 is a top plan view partially broken away of a two piece specimen support and specimen conveyor means.
Figure 14:
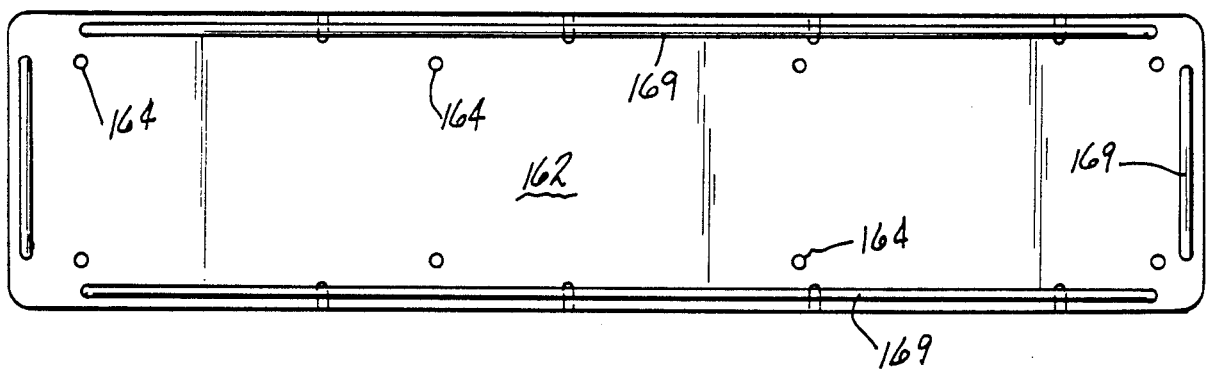
FIG. 14 is a top plan view of the bottom piece part of the two piece conveyor means of FIG. 13.

The top plate 163 is formed with an opening 173 and a plurality of depending, longitudinally extending ribs 168—168 to provide stiffness and bear upon a pad of absorbant material 165 sandwiched between the top and bottom plates of the conveyor means 123 as is most apparent in FIGS. 7 and 13.

The bottom plate is formed further with a discontinuous, peripheral bead 169 which is received within the interior of the top plate making a snug fit of the inner surface of top plate sidewalls 171.

Figure 15:
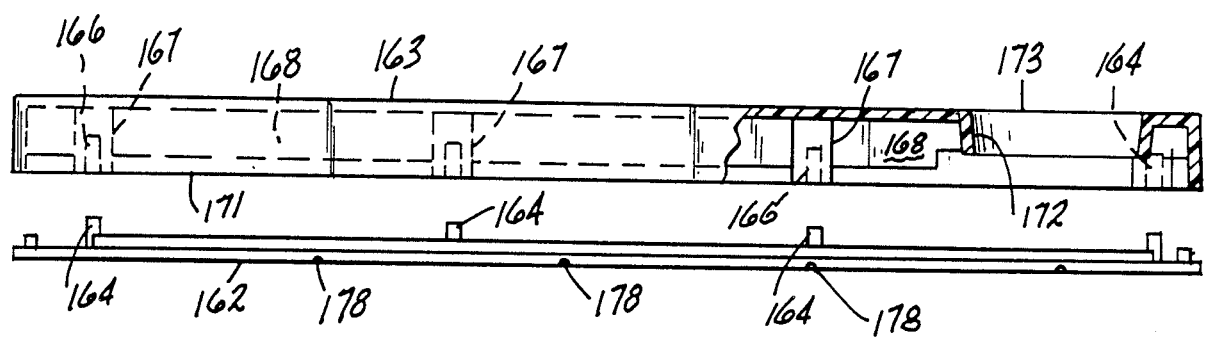
FIG. 15 is a side view, partially in section, showing the top and bottom piece parts of the conveyor means spaced apart for clarity.
Figure 16:
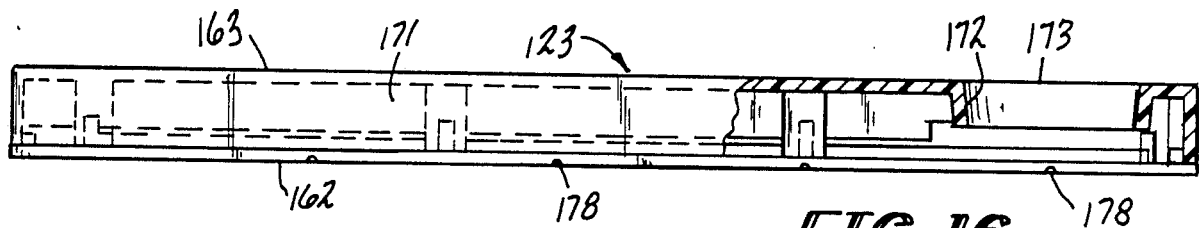
FIG. 16 shows the piece parts of FIG. 15 assembled.

The right ends of the ribs 168 are cut-out or notched as is apparent in FIGS. 15 and 16 to accommodate the depending flange 172 of the opening 173 and to accommodate a filter, porous disk, spacer or the like as shown at 174 in FIG. 7.

It is to be understood that use of a spacer at 174 is purely optional and the device is designed to provide clearance for the disk should a particular test or assay so require.

Normally a specimen support 113 spans the bottom of the opening 173 as shown in FIG. 7 fastened to the outlet of the opening (flange 172) in any suitable fashion.

The pad of absorbant material 165 is of generally rectangular configuration and is dimensioned so that it is received with the bounds of the posts 167 as shown in FIG. 13. The thickness of the pad 165 is selected so that when the conveyor means 123 is assembled the pad is compressed lightly.

LOADING OR CHARGING THE BLISTER PACK

After the blister pack has been formed to create blisters 138, 139 and 141 with a punch means 143, 144 and 146, respectively, the formed unit is placed on a generally flat surface with the open blisters and apices of the punch means facing upwardly. Appropriate liquid reagents including water are introduced in the various blisters. Thereafter a foil or film 147 is applied to the open blisters sealing the blisters to make them liquid tight and to define containers 114, 116 and 117 of FIG. 6.

Next the charged blister pack 142 is inserted (nested) into housing 111 so that each blister 138, 139, 141 is received in mating openings 134, 136 or 137 (FIG. 8), respectively. FIG. 7 shows blister 141 received in mating opening 137 and in corresponding fashion blisters 138, 139 and received in opening 134 and 136, respectively.

Note that in FIG. 1 blisters 138, 139 and 141 are designated liquid containers 114, 116 and 117 and punches 143, 144 and 146 are designated punch means 118, 119 and 121.

ASSEMBLING

The blister pack 142 can be secured to the housing 111 by adhesive or the like, or, as in the disclosed embodiment, left unsecured. Next the assembled conveyor means 123 is inserted into the housing guided by the track means 132-133. The thickness of the conveyor means is such that it bears slidably upon the flats 176 (FIG. 12) of the blister pack to retain the pack nested in the housing.

OPERATION

After the specimen support means 113 has been innoculated with a test specimen and after an appropriate time delay (depending upon instructions for the particular test being conducted) the left end of FIG. 1 of the conveyor means 123 is grasped manually and withdrawn to the left relative to the housing until the specimen support means is transported to a point directly beneath liquid container 117 which includes blister 141.

Proper register is achieved by the use of detents means such as a protuberance 177 formed on track 133 (see FIGS. 7 and 9) and a series of mating indentations 178 formed on the bottom of the conveyor means (see FIGS. 15 and 16).

Figure 17:
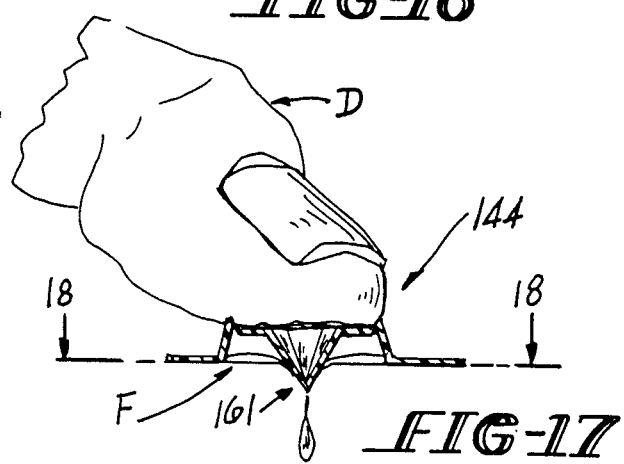
FIG. 17 shows the manually operable punch means piercing or rupturing a foil or film to release liquid from the blister, container or receptacle.

After the conveyor means "clicks" into position, a suitable digit D or (other instrumentality) is used to apply pressure to the flexible top of the blister portion of the liquid container C whereupon the punch means P operates to rupture, burst or tear the foil of film F to release liquid as shown in FIG. 17.

This occurrence causes liquid to rain upon the test specimen below carried by the conveyor means.

In accordance with instructions the conveyor means is indexed in sequence to the succeeding container and the steps just described are again undertaken to release fluid from each container.

Figure 18:
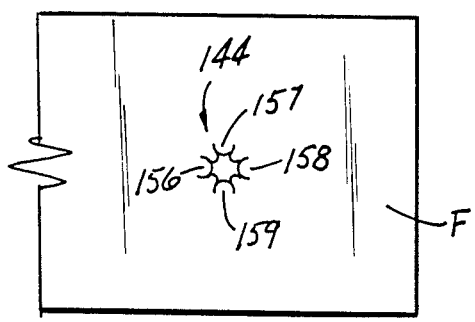
FIG. 18 is a transverse sectional view of FIG. 17 as viewed in the plane of the line 18—18 and in the direction of the arrows.

FIG. 18 is a transverse section of FIG. 17 in the plane of line 18—18 as viewed in the direction of the arrows.

The advantage of the grooved conical punch terminating in a sharp point insures that (1) the foil or film F will be pierced readily and (2) the liquid will flow past the punch freely. It has been found that a uniform (ungrooved) lateral surface of a cone shape While effective to puncture tends to block or plug the punctured opening inhibiting the flow of fluid.

The language "seamless" is intended to denote that the punch means is a contiguous part of the blister and to indicate that the punch means has never existed as a separate piece.

Furthermore, it is not intended that the punch means be limited to a conic configuration or that it be limited to a central location on the blister body.

As stated earlier the present invention, in its rotary or linear form, is not intended to be limited to the number of liquid containers or liquid receptacles shown; the number of containers is a matter of choice depending upon the particular test, immunoassay or diagnosis procedure in either medical or veterinary applications.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. A hand held assay device comprising:
   a housing means,
   a movable transport means within the housing means,
   at least one liquid container within said housing means,
   said container comprising a molded, flexible blister having an open side,
   closure means spanning said open side to close and seal said blister,
   punch means molded integrally with said blister defining with said blister a single, unitary, seamless piece part,
   said punch means defining a cone having a base, a lateral surface and an apex,
   the lateral surface of said cone being interrupted by a plurality of grooves of varying depth extending from said base to said apex,
   the depth of said grooves being greatest at the base of said cone graduating to zero depth at the apex, and
   said cone being operable in response to deformation of the blister to rupture the closure means whereby said cone, by virtue of said grooves, is operable to release liquid from said container in a predictable manner.

2. The device of claim 1 in which the housing is formed with a plurality of apertures,
   a corresponding number of said containers disposed within the housing,
   each container being individual to a mating aperture,
   a specimen support disposed upon said transport means,
   said transport means being movable relative to the housing and relative to the containers whereby sequential rupturing of the containers is operable to dispense fluid to a specimen carried by said support means in step by step fashion.

3. The device of claim 2 in which the housing and the transport means include cooperating detent means for facilitating indexing the transport means and its specimen support into registration with the apertures.

4. A liquid container for use in an assay or diagnostic device comprising:
   a molded, flexible blister having an open side,
   closure means spanning said open side to close and seal said blister,
   a punch means molded integrally with said blister defining with said blister a single, unitary, seamless piece part,
   said punch means defining a cone having a base, a lateral surface and an apex,
   the lateral surface of said cone being interrupted by a plurality of grooves of varying depth extending from said base to said apex,
   the depth of said grooves being greatest at the base of said cone graduating to zero depth at the apex,
   said cone being operable in response to deformation of the blister to rupture the closure means whereby said cone, by virtue of said grooves, is operable to release liquid from said container in a predictable manner.

* * * * *